United States Patent [19]

Davidson et al.

[11] Patent Number: 5,300,524
[45] Date of Patent: Apr. 5, 1994

[54] SPIROCYCLIC PAF ANTAGONISTS

[75] Inventors: Alan H. Davidson, Witney; Mark Whittaker, Old Marston; Zoe M. Spavold, Witney, all of England

[73] Assignee: British Bio-Technology Limited, Oxford, England

[21] Appl. No.: 760,726

[22] Filed: Sep. 16, 1991

[30] Foreign Application Priority Data

Mar. 6, 1991 [GB] United Kingdom ............... 9104746

[51] Int. Cl.[5] ..................... A61K 31/34; C07D 311/96
[52] U.S. Cl. ..................... 514/462; 549/331
[58] Field of Search .................. 549/331; 514/462

[56] References Cited

FOREIGN PATENT DOCUMENTS 0144804 11/1984 European Pat. Off. .
0238202 2/1987 European Pat. Off. .

*Primary Examiner*—Alan L. Rotman
*Assistant Examiner*—A. Owens
*Attorney, Agent, or Firm*—Allegretti & Witcoff, Ltd.

[57] ABSTRACT

Compounds of general formula I;

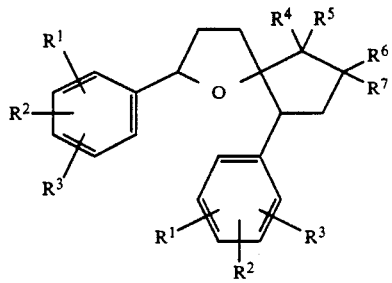

wherein
$R^1$, $R^2$, $R^3$, $R^4$, $R^5$, $R^6$, and $R^7$ are variables.

These compounds are antagonists of platelet activating factor (PAF) and as such are useful in the treatment or amelioration of various diseases or disorders mediated by PAF.

18 Claims, No Drawings

SPIROCYCLIC PAF ANTAGONISTS

This invention relates primarily to novel compounds which are antagonists of platelet activating factor.

Platelet Activating Factor (PAF) is a bioactive phospholipid which has been identified as 1-O-hexadecyl-/octadecyl-2-acetyl-sn-glyceryl-3-phosphoryl choline. PAF is released directly from cell membranes and mediates a range of potent and specific effects on target cells resulting in a variety of physiological responses which include hypotension, thrombocytopenia, bronchoconstriction, circulatory shock, and increased vascular permeability (oedema/erythema). It is known that these physiological effects occur in many inflammatory and allergic diseases and PAF has been found to be involved in a number of such conditions including asthma, endotoxin shock, glomerulonephritis, immune regulation, tranplant rejection, gastric ulceration, psoriasis, cerebral, myocardial and renal ischemia. Thus the compounds of the invention, by virtue of their ability to antagonise the actions of PAF, should be of value in the treatment of any of the above conditions.

Compounds which have been disclosed as possessing activity as PAF antagonists include compounds which are structurally related to the PAF molecule such as glycerol derivatives (EP-A-0238202), and heterocyclic compounds such as 2,5-diaryl tetrahydrofurans (EP-A-0144804).

The compounds of the present invention differ from PAF antagonists such as the 2,5-diaryltetrahydrofurans, in that they are substituted spiro cyclic derivatives. The present invention provides novel and useful substituted spirocyclic derivatives and their pharmaceutically acceptable acid addition salts, and pharmaceutical uses thereof as PAF antagonists.

According to a first aspect of the invention there is provided a compound of general formula I;

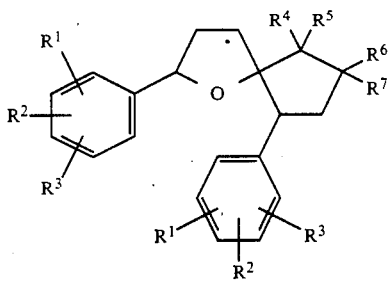

I wherein:

each of $R^1$, $R^2$, and $R^3$ independently represents hydrogen, $C_1$–$C_6$ alkyl, $C_2$–$C_6$ alkenyl, $C_1$–$C_6$ alkoxy, $C_1$–$C_6$ thioalkyl, halo, CN, $NO_2$, $SOC_1$–$C_6$ alkyl, $SO_2C_1$–$C_6$ alkyl, $SO_2NH_2$, $COC_1$–$C_6$ alkyl, CHO, $COOC_1$–$C_6$ alkyl, $CH_2OH$, benzyl, benzoyl, $CF_3$, $CONH_2$, $NHCOC_1$–$C_6$ alkyl;

each of $R^4$ and $R^5$ independently represents hydrogen, $C_1$–$C_6$ alkyl, $C_2$–$C_6$ alkenyl, $C_1$–$C_6$ alkoxy, $C_1$–$C_6$ thioalkyl, halo, CN, $NO_2$, $SOC_1$–$C_6$ alkyl, $SO_2C_1$–$C_6$ alkyl, CHO, $COOC_1$–$C_6$ alkyl, $CH_2OH$, OH, Benzyl, Benzoyl, $CF_3$, $CONH_2$, $NHCOC_1$–$C_6$ alkyl or a OC(=O)$R^8$ group wherein $R^8$ represents $C_1$–$C_6$ alkyl, $C_2$–$C_6$ alkenyl, $C_1$–$C_6$ alkoxy, $C_1$–$C_6$ thioalkyl, $COC_1$–$C_6$ alkyl, $COOC_1$–$C_6$ alkyl, benzyl, benzoyl, nitrile, $CF_3$ or a V group wherein V represents a) a group

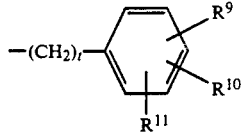

wherein t is an integer from 0 to 3 and each of $R^9$, $R^{10}$ and $R^{11}$ is independently hydrogen, $C_1$–$C_6$ alkyl, $C_2$–$C_6$ alkenyl, $C_1$–$C_6$ alkoxy, $C_1$–$C_6$ thioalkyl, halo, CN, $NO_2$, $SOC_1$–$C_6$ alkyl $SO_2C_1$–$C_6$ alkoxy, $SO_2NH_2$, COOH, $COC_1$–$C_6$ alkyl, CHO, $COOC_1$–$C_6$ alkyl, $CH_2OH$, OH, benzyl, benzoyl, $CF_3$, $CONH_2$, $NHCOC_1$–$C_6$ alkyl; b) a group —$(CH_2)_s$—Y wherein s is an integer from 0 to 5 and Y represents a 5- or 6-membered aromatic heterocyclic ring containing one or more sp2 nitrogen atoms in its ring, which heterocyclic ring may be optionally fused to a benzene ring or to a further 5- or 6-membered aromatic heterocyclic ring containing one or more nitrogen atoms, wherein at least one of the said heterocyclic rings may also contain an oxygen or sulphur atom, and wherein any of the rings may be optionally substituted with one or more substituents selected from $C_1$–$C_6$ alkyl, $C_1$–$C_6$ alkoxy, halo, $CF_3$ and CN;

or $R^4$ together with $R^5$ forms a =O, =N-OH, =$NHR^8$ or =$CHR^8$ group, wherein $R^8$ is as defined above;

each of $R^6$ and $R^7$ independently represents hydrogen, $C_1$–$C_6$ alkyl, $COC_1$–$C_6$ alkyl, benzyl, a group V as defined above or a COV group wherein V is as defined above;

or $R^6$ together with $R^7$ form a =$CR^{12}R^{13}$ group wherein each of $R^{12}$ and $R^{13}$ independently represent a hydrogen atom, a $C_1$–$C_{18}$ alkyl, a $C_2$–$C_6$ alkenyl, pyrrole or a group V as defined above;

Hereafter in this specification the term "compound" includes "salt" or "hydrate" unless the context requires otherwise.

As used herein the term "halo" means fluoro, chloro, bromo or iodo.

As used herein the term "$C_1$–$C_6$ alkyl" refers to straight chain or branched chain hydrocarbon groups having from one to six carbon atoms. Illustrative of such alkyl groups are methyl, ethyl, propyl, isopropyl, butyl, isobutyl, sec-butyl, tertbutyl, pentyl, neopentyl and hexyl.

As used herein the term "$C_2$–$C_6$ alkenyl" refers to straight chain or branched chain hydrocarbon groups having from two to six carbon atoms and having in addition one double bond, of either E or Z stereochemistry where applicable. This term would include for example, vinyl, 1-propenyl, 1- and 2-butenyl and 2-methyl-2-propenyl.

As used herein the term "$C_1$–$C_6$ alkoxy" refers to straight chain or branched chain alkoxy groups having from one to six carbon atoms. Illustrative of such alkoxy groups are methoxy, ethoxy, propoxy, isopropoxy, butoxy, isobutoxy, sec-butoxy, tert-butoxy, pentoxy, neopentoxy and hexoxy.

As used herein the term "$C_1$–$C_6$ thioalkyl" refers to straight chain or branched chain alkylthio groups having from one to six carbon atoms. Illustrative of such alkyl groups are methylthio, ethylthio, propylthio, isopropylthio, butylthio, isobutylthio, sec-butylthio, tertbutylthio, pentylthio, neopentylthio and hexylthio.

As used herein the term $C_1$–$C_{18}$ alkyl refers to straight chain or branched chain hydrocarbon groups having from one to eighteen carbon atoms. Illustrative of such alkyl groups are methyl, ethyl, propyl, isopropyl, butyl, isobutyl, sec-butyl, tertbutyl, pentyl, neopentyl, hexyl, decyl, dodecyl, tridecyl, tetradecyl, pentadecyl, hexadecyl, heptadecyl and octadecyl. From one to eight carbon atoms may be preferred.

In compounds of this invention, the presence of several asymmetric carbon atoms gives rise to diastereoisomers, each of which consists of two enantiomers, with the appropriate R or S stereochemistry at each chiral center. The invention is understood to include all such diastereoisomers, their optically active enantiomers and mixtures thereof.

The term "pharmaceutically or veterinarily acceptable acid addition salt" refers to a salt prepared by contacting a compound of formula (I) with an acid whose anion is generally considered suitable for human or animal consumption.

Examples of pharmaceutically and/or veterinarily acceptable acid addition salts include the hydrochloride, sulphate, phosphate, acetate, propionate, lactate, maleate, succinate and tartrate salts.

Preferred compounds include those in which, independently or in any compatible combination:

$R^1$ represents a $C_1$-$C_6$ alkoxy (for example methoxy) group;

$R^2$ represents a hydrogen atom or a $C_1$-$C_6$ alkoxy (for example methoxy) group;

$R^3$ represents a hydrogen atom;

$R^4$ represents a hydroxyl group, a OC(=O)$R^8$ group or together with $R^5$ forms a =O or =CHR$^8$ group;

$R^5$ represents a hydrogen atom or together with $R^4$ forms a =O or =CHR$^8$ group;

$R^6$ represents a hydrogen atom, a group V, a group COV or together with $R^7$ forms =CR$^{12}$R$^{13}$ group;

$R^7$ represents a hydrogen atom or together with $R^6$ forms =CR$^{12}$R$^{13}$ group;

$R^8$ represents a nitrile group or a group V;

V represents a

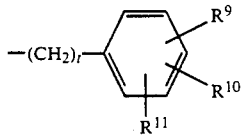

group or a —(CH$_2$)$_s$—Y group;

t represents an integer of 0 or 1;

$R^9$ represents a hydrogen atom, a $C_1$-$C_6$ alkoxy (for example methoxy) group, a halogen (for example chloro) atom or a nitro group;

$R^{10}$ represents a hydrogen atom, a $C_1$-$C_6$ alkoxy (for example methoxy) group' or a nitro group;

$R^{11}$ represents a hydrogen atom or a $C_1$-$C_6$ alkoxy (for example methoxy) group;

s represents an integer of 0, 1, 2 or 4;

Y represents a pyridyl (for example 2-pyridyl, 3-pyridyl or 4-pyridyl) group;

$R^{12}$ represents a $C_1$-$C_{18}$ alkyl (for example methyl, t-butyl or heptyl) group; a pyrrole (for example 2-pyrrole) group or a group V;

$R^{13}$ represents a hydrogen atom or a $C_1$-$C_{18}$ (for example methyl) group;

Particularly preferred compounds include:

1. 1-Oxa-6-oxo-2,9-di(3,4-dimethoxyphenyl)spiro[4,4]nonane,
2. 1-Oxa-6-oxo-7-(3-pyridyl)methylene-2,9-di(3,4-dimethoxyphenyl)spiro[4,4]nonane,
3. 1-Oxa-6-oxo-7-(2-pyridyl)methylene-2,9-di(3,4-dimethoxyphenyl)spiro[4,4]nonane,
4. 1-Oxa-6-oxo-7-(4-pyridyl)methylene-2,9-di(3,4-dimethoxy-phenyl)spiro[4,4]nonane,
5. 1-Oxa-6-oxo-7-(3-chlorophenyl)methylene-2,9-di(3,4-dimethoxyphenyl)spiro[4,4]nonane,
6. 1-Oxa-6-oxo-7-(3,4,5-trimethoxyphenyl)methylene-2,0-di (3,4-dimethoxyphenyl)spiro[4,4]nonane,
7. 1-Oxa-6-oxo-7-dimethylmethylene-2,9-di(3,4-dimethoxyphenyl)spiro[4,4]nonane,
8. 1-Oxa-6-oxo-7-tert-butylmethylene-2,9-di(3,4-dimethoxyphenyl)spiro[4,4]nonane,
9. 1-Oxa-6-oxo-7-heptylmethylene-2,9-di(3,4-dimethoxyphenyl)spiro[4,4]nonane,
10. 1-Oxa-6-oxo-7-(3-pyridylethyl)methylene-2,9-di(3,-4-dimethoxyphenyl)spiro[4,4]nonane,
11. 1-Oxa-6-oxo-7-(3-pyridylbutyl)methylene-2,9-di(3,4-dimethoxyphenyl)spiro[4,4]nonane,
12. 1-Oxa-6-oxo-7-(3-pyrrolyl)methylene-2,9-di(3,4-dimethoxyphenyl)spiro[4,4]nonane,
13. 1-Oxa-6-oxo-7-benzoyl-2,9-di(3,4-dimethoxyphenyl)spiro[4,4]nonane,
14. 1-Oxa-6-oxo-7-(2-pyridyl)methyl-2,9-di(3,4-dimethoxyphenyl)spiro[4,4]nonane,
15. 1-Oxa-6-hydroxy-2,9-di(3,4-dimethoxyphenyl)-spiro[4,4]nonane,
16. 1-Oxa-6-(3,5-dinitro)benzoyloxy-2,9-di(3,4-dimethoxyphenyl)spiro[4,4]nonane,
17. 1-Oxa-6-cyanomethylene-2,9-di(3,4-dimethoxyphenyl)spiro-[4,4]nonane,
18. 1-Oxa-6-oxo-2,9-di(4-methoxyphenyl)spiro[4,4]nonane,
19. 1-Oxa-6-oxo-7-(3-pyridyl)methylene-2,9di(4-methoxyphenyl)spiro[4,4]nonane.

Compounds of general formula I may be prepared by any suitable method known in the art and/or by the following process, which itself forms part of the invention.

According to a second aspect of the invention, there is provided a process for preparing a compound of general formula I as defined above, the process comprising:

a) treating a sulphonyl derivative represented by the general formula II

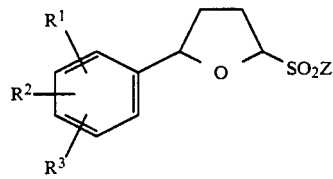

wherein $R^1$, $R^2$ and $R^3$ are as defined in general formula I and Z is phenyl or substituted phenyl (e.g. 4-methylphenyl), with a strong organic non nucleophilic base (e.g. lithium diisopropyl amide) followed by an organic proton source (e.g. tert-butyl bromide);

b) treating a sulphonyl derivative represented by the general formula II, wherein $R^1$, $R^2$ and $R^3$ are as defined in general formula I and Z is phenyl or substituted phenyl (e.g. 4-methylphenyl), with a strong organic non nucleophilic base (e.g. lithium diisopropyl amide) followed by a carbonyl derivative of general formula III

OCR$^{12}$R$^{13}$      III wherein R$^{12}$ and R$^{13}$ are as defined in general formula I;

c) treating a sulphonyl derivative represented by the general formula II, wherein R$^1$, R$^2$ and R$^3$ are as defined in general formula I and Z is phenyl or substituted phenyl (e.g. 4-methylphenyl), with a strong organic non nucleophilic base (e.g. lithium diisopropyl amide) followed by a carboxylic acid halide derivative of general formula IV HalC(=O)V      IV wherein V is as defined in general formula I and Hal is fluoro, chloro, bromo or iodo;

d) optionally after step (a), step (b) or step (c) converting, in one or a plurality of steps, a compound of general formula I into another compound of general formula I.

The reactions of steps (a), (b) and (c) can for preference be conducted in an aprotic solvent, preferably tetrahydrofuran, to yield compounds of general formula I. The products of general formula I, obtained from step (a), (b) or (c) will be mixtures of one or more pairs of diastereoisomers. These may be separated by physical methods (e.g. flash chromatography).

By means of step (d) compounds of general formula I may be prepared by the treatment of a compound of general formula I wherein R$^4$ together with R$^5$ forms a =O group and R$^6$ and R$^7$ are hydrogen atoms, with a strong organic non nucleophilic base (e.g. lithium diisopropyl amide) in an aprotic solvent (e.g. tetrahydrofuran) followed by an electrophile of general formula III or general formula IV.

Also by means of step (d) compounds of general formula I wherein R$^4$ together with R$^5$ forms a =CHR$^8$ group may be prepared by the treatment of a compound of general formula I wherein R$^4$ together with R$^5$ forms a =O group and R$^6$ and R$^7$ are hydrogen atoms, with an organometallic reagent of general formula V LiCH$_2$R$^8$      V wherein R$^8$ is as defined in general formula I.

Also by means of step (d) compounds of general formula I wherein R$^4$ is hydroxyl and R$^5$ is a hydrogen atom may be prepared by treatment of a compound of general formula I wherein R$^4$ together with R$^5$ forms a =O group, with a reducing agent (e.g. sodium borohydride).

Also by means of step (d) compounds of general formula I wherein R$^4$ is a OC(=O)R$^8$ group and R$^5$ is a hydrogen atom may be prepared by the treatment of a compound of general formula I wherein R$^4$ is a hydroxyl group and R$^5$ is a hydrogen atom with an acid halide of general formula VI HalC(=O)R$^8$      VI wherein R$^8$ is as defined in general formula I and Hal is fluoro, chloro, bromo or iodo.

Also by means of step (d) compounds of general formula I wherein R$^6$ is a group V and R$^7$ is a hydrogen atom may be prepared by the treatment of a compound of general formula I wherein R$^4$ together with R$^5$ is a =O group and R$^6$ together with R$^7$ is a =CR$^{12}$R$^{13}$ group with sodium hydrogen telleuride.

Sulphonyl derivatives of general formula II may be prepared by a number f methods. The first method for the preparation of sulphonyl derivatives of general formula II, wherein R$^1$, R$^2$ and R$^3$ are as defined in general formula I and Z is phenyl or substituted phenyl (e.g. 4-methylphenyl), involves treatment of a lactol of general formula VII

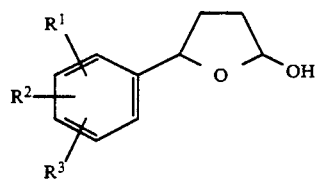

wherein R$^1$, R$^2$ and R$^3$ are as defined in general formula I with a sulphinic acid of general formula VIII

ZSO$_2$H      VIII wherein Z is a phenyl or substituted phenyl group, and powdered calcium chloride in dichloromethane.

Lactol derivatives of general formula VII are available in the art or may be prepared by methods, known to those skilled in the art, which includes the reduction of a lactone of general formula IX

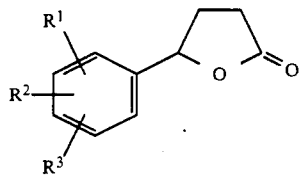

wherein R$^1$, R$^2$ and R$^3$ are as defined in general formula I, with a suitable reducing agent (e.g. diisobutylaluminium hydride) in an appropriate solvent (e.g. toluene). Sulphinic acids of general formula VIII are available in the art or may be prepared by methods analogous to those known in the art. Lactones of general formula IX are available in the art or may be prepared by methods analogous to those known in the art.

In a second method sulphonyl derivatives of general formula II, wherein R$^1$, R$^2$ and R$^3$ are as defined in general formula I and Z is phenyl or substituted phenyl (e.g. 4-methylphenyl), may be prepared by treatment of a lactol ether of general formula X

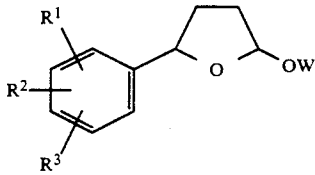

wherein R$^1$, R$^2$ and R$^3$ are as defined in general formula I and W is C$_1$-C$_6$ alkyl with a sulphinic acid of general formula VIII.

Lactol ethers of general formula X are available in the art or may be prepared by methods, known to those skilled in the art, which includes the following procedures. The first method involves reaction of a lactol of general formula VII, wherein R$^1$, R$^2$ and R$^3$ are as defined in general formula I, with an alcohol of general formula XI

HW      XI wherein W is $C_1$–$C_6$ alkoxy, in the presence of one equivalent of trifluoroacetic anhydride. Alcohols of general formula XI are available in the art.

In a second method lactol ethers of general formula X may be prepared by the treatment of an cyclic ether derivative of general formula XII

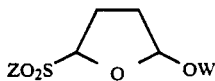
XII wherein W is a $C_1$–$C_6$ alkyl group and Z is phenyl or substituted phenyl, with a grignard reagent of general formula XIII

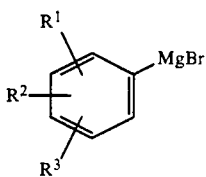
XIII wherein $R^1$, $R^2$ and $R^3$ are as defined in general formula I, in the presence of anhydrous zinc bromide in dry tetrahydrofuran.

Cyclic ether derivatives of general formula XII may be prepared by the treatment of a bis-ether of general formula XIV

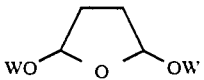
XIV wherein W is $C_1$–$C_6$ alkyl with one equivalent of a sulphinic acid of general formula VIII and powdered calcium chloride in dichloromethane. Grignard reagents of general formula XI may be prepared by methods known to those skilled in the art. Bisethers of general formula XIV are available in the art or may be prepared by methods analogous to those known in the art.

In a third method lactol ethers of general formula X may be prepared by the treatment of an unsaturated cyclic ether of general formula XV

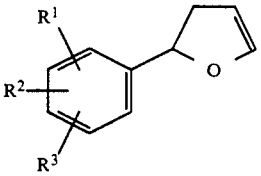
XV wherein $R^1$, $R^2$ and $R^3$ are as defined in general formula I, with an alcohol of general formula XI in the presence of an acid catalyst (e.g. p-toluenesulphonic acid). Unsaturated cyclic ethers of general formula XV are available in the art or may be prepared by methods analogous to those known in the art.

In a third method sulphonyl derivatives of general formula II, wherein $R^1$, $R^2$ and $R^3$ are as defined in general formula I and Z is phenyl or substituted phenyl, may be prepared by treatment of an unsaturated cyclic ether of general formula XIV, wherein $R^1$, $R^2$ and $R^3$ are as defined in general formula I, with a sulphinic acid of general formula VIII.

In a fourth method sulphonyl derivatives of general formula II, wherein $R^1$, $R^2$ and $R^3$ are as defined in general formula I and Z is phenyl or substituted phenyl, may be prepared by treatment of a bis-sulphone of general formula XVI

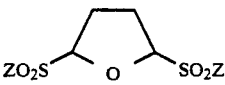
XVI wherein Z is a phenyl or substituted phenyl group with one equivalent of a grignard reagent of general formula XIII in the presence of anhydrous zinc bromide in dry tetrahydrofuran.

Bis-sulphones of general formula XVI may be prepared by the reaction of a bis-ether of general formula XIV with two equivalents of benzenesulphinic acid and powdered calcium chloride in dichloromethane.

Carbonyl derivatives of general formula III are either known compounds or can be prepared conventionally (e.g. by the methods described for the preparation of the Examples).

Carboxylic acid halides of general formula IV are available in the art or can be prepared by methods known to those skilled in the art.

Organometallic reagents of general formula V are available in the art or can be prepared by methods known to those skilled in the art.

The appropriate solvents employed in the above reactions are solvents wherein the reactants are soluble but do not react with the reactants. The preferred solvents vary from reaction to reaction and are readily ascertained by one of ordinary skill in the art.

Compound of general formula II is a valuable intermediate in the preparation of compounds of general formula I, as are other novel compounds specifically or generically disclosed herein. According to a third aspect of the invention, there is therefore provided a compound of general formula II.

This invention also relates to a method of treatment for patients (or animals including mammalian animals raised in the dairy, meat, or fur trade or as pets) suffering from disorders or diseases which can be attributed to PAF as previously described, and more specifically, a method of treatment involving the administration of PAF antagonists of general formula I as the active ingredient. In addition to the treatment of warm blooded animals such as mice, rats, horses, cattle, pigs, sheep, dogs, cats, etc., the compounds of the invention are effective in the treatment of humans.

According to a fourth aspect of the invention there is provided a compound of general formula I for use in human or veterinary medicine particularly in the management of diseases mediated by PAF; compounds of general formula I can be used among other things to reduce inflammation and pain, to correct respiratory, cardiovascular, and intravascular alterations or disorders, and to regulate the activation or coagulation of platelets, to correct hypotension during shock, the pathogenesis of immune complex deposition and smooth muscle contractions.

According to an fifth aspect of the invention there is provided the use of a compound of general formula I in the preparation of an agent for the treatment of PAF-mediated diseases; and/or the treatment of inflammation such as rheumatoid arthritis, osteoarthritis and eye inflammation, cardiovascular disorder, thrombocytopenia, asthma, endotoxin shock, glomerulonephritis, immune regulation, psoriasis.

Compounds of general formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

According to a sixth aspect of the invention there is provided a pharmaceutical or veterinary formulation comprising a compound of general formula I and a pharmaceutically and/or veterinarily acceptable carrier. One or more compounds of general formula I may be present in association with one or more non-toxic pharmaceutically and/or veterinarily acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occuring phosphatide, for example lecithin, or condensation products of an alkylene oxide with fatty acids for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical application to the skin compounds of general formula I may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

For topical applications to the eye, compounds of general formula I may be made up into a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorhexidine, and thickening agents such as hypromellose may also be included Compounds of general formula I may be administered parenterally in a sterile medium. The drug depending on the vehicle and concentration used, can either be suspended or dissolved in the vehicle. Advantageously, adjuvants such as a local anaesthetic, preservative and buffering agents can be dissolved in the vehicle.

Compounds of general formula I may be used for the treatment of the respiratory tract by nasal or bucal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Dosage levels of the order of from about 0.1 mg to about 140 mg per kilogram of body weight per day are useful in the treatment of the above-indicated conditions (about 0.5 mg to about 7 g per patient per day). For example, inflammation may be effectively treated by the administration of from about 0.01 to 50 mg of the compound per kilogram of body weight per day (about 1.0 mg to about 3.5 g per patient per day). The dosage employed for the topical administration will, of course, depend on the size of the area being treated. For the eyes each dose will be typically in the range from 10 to 100 mg of the drug.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

It has, been found that the compounds of general formula I exhibit in vitro antagonistic activities with respect to PAF. Compounds of general formula I inhibit PAF-induced functions in both the cellular and tissue levels by changing the PAF binding to its specific receptor site. The ability of compounds of general formula I to inhibit the binding of PAF to its specific receptor binding site on human platelet plasma membranes was measured according to Pharmacological Example 1. The ability of compounds of general formula I to reverse the hypotension caused by an infusion of PAF in rats was measured according to Pharmacology Example 2.

The following examples illustrate the invention, but are not intended to limit the scope in any way.

The following abbreviations have been used in the Examples:
DCM—Dichloromethane
DIPE—Diisopropylether
THF—Tetrahydrofuran

EXAMPLE 1

1-Oxa-6-oxo-2,9-di(3,4-dimethoxyphenyl)spiro[4,4]nonane

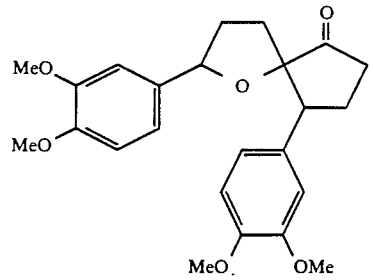

(a) 2-Benzenesulphonyl-5-methoxytetrahydrofuran 2,5-Dimethoxytetrahydrofuran (17.1 ml, 0.13 M) was added dropwise to a stirred solution of benzenesulphinic acid (17.0 g, 0.12 M) in dry DCM (100ml) containing a suspension of powdered $CaCl_2$ (1.0 g) at room temperature under argon. After 4 h, the solution was washed with water (2×50 ml), dried ($Na_2SO_4$) and evaporated. The product was crystallised (diethyl ether/hexane) to give 2-benzenesulphonyl-5-methoxytetrahydrofuran (15 9 g, 55%).

White crystalline solid: m.p. 68° C.

$delta_H$ (250 MHz, $CDCl_3$) 7.94 (2H, m), 7.68 (1H, m), 7.57 (2H, m), 5.22 (0.5H, m), 5.12 (0.5H, m), 4.98 (0.5H, m), 3.37, 3.30 (3H, 2s), 2.64–2.33 (2H, m), 2.06–1.83 (2H, m).

(b)
2-(3,4-Dimethoxyphenyl)-5-methoxytetrahydrofuran

Magnesium (2.18 g, 0.091 M) was placed in a 3-necked flask containing dry THF (10 ml) and 1,2-dibromoethane (0.2 ml). A solution of 4-bromoveratrole (18.0 g, 0.086 M) in THF (50 ml) was added dropwise, warming to initiate reaction. The resulting solution was heated at reflux for 0.75 h then cooled to room temperature and cannulated into a 1M solution of $ZnBr_2$ in THF (50 ml, 0.05 M) and stirred for 0.5 h at room temperature. A solution of 2-benzenesulphonyl-5-methoxytetrahydrofuran (10.0 g, 0.041 M) in THF (50 ml) was added dropwise to the pale yellow suspension and the mixture allowed to stir at room temperature for 20 h. Reaction was quenched by addition of 1N HCl (50 ml), and extracted with ether (2×100 ml). The organics were combined washed with water (50 ml) dried ($Na_2SO_4$) and evaporated. Flash column chromatography (flash silica gel, hexane:ethyl acetate (3:2)) gave 2-(3,4-dimethoxyphenyl)-5-methoxytetrahydrofuran (8.0 g, 82%) as a yellow oil (rf 0.28).

$delta_H$(250 MHz, $CDCl_3$) 7.96 (1H, m), 7.58 (2H, m), 5.33 (0.5H, dd), 5.13 (0.5H, d), 4.98 (0.5H, m), 3.96 (3H, s, OMe), 3.90 (3H, s, OMe), 3.85 (3H, s, OMe), 2.53 (2H, m), 2.34 (2H, m).

(c)
2-Benzenesulphonyl-5-(3,4-dimethoxyphenyl)tetrahydrofuran

To a solution of benzenesulphinic acid (8.68 g, 0.061 M) in DCM (120 ml) containing a suspension of $CaCl_2$ (1.0 g) at room temperature was added a solution of 2-(3,4,dimethoxybenzyl)-5-methoxytetrahydrofuran (7.0 g, 0.029 M) in $CH_2Cl_2$ (80 ml). The mixture was stirred at room temperature for 4 h, quenched by washing with water (2×50 ml), dried ($Na_2SO_4$) and evaporated. Column chromatography (flash silica gel, hexane:ethyl acetate (3:2)) provided the product (Rf 0.3) as a clear oil which was crystallised from ethyl acetate/hexane to give 2-benzenesulphonyl-5-(3,4-dimethoxyphenyl)tetrahydrofuran (3.5 g, 35%).

Off white crystalline solid: m.p. 107–106° C.
Analysis calculated for $C_{18}H_{20}O_5S$.
Requires C 62.05 H 5.79 S 9.20.
Found C 62.12 H 5.79 S 9.36.
i.r. (KBr) 2960, 1590, 1510 $cm^{-1}$ $delta_H$ (250 MHz, $CDCl_3$) 7.95 (2H, m), 7.66-7.51 (3H, m), 7.35 (0.5H, d, J 1.9 Hz), 6.96 (0.5H, dd, J 8.2, J 1.9 Hz), 6.82 (3H, t, J 8.2 Hz), 5.31 (0.5H, dd,), 5.14 (0.5H, dd, J 7.7, J 5.3 Hz), 4.97 (1H, m), 3.97 (1.5H, s), 3.91 (1.5H, s) 3.86 (3H, s), 2.80–1.60 (4H, m).

(d)
1-Oxa-6-oxo-2,9-(3,4-dimethoxyphenyl)spiro[4,4]nonane

To a solution of 2-benzenesulphonyl-5-(3,4-dimethoxyphenyltetrahydrofuran (350 mg, 1.0 mmol) in THF (10 ml) at −78° C., was added a 1.5 M solution of lithium diisopropylamide in hexane (1 ml, 1.5 mmol) and the resulting solution stirred at −78° C. for 15 min. tert-Butyl bromide (0.23 ml, 2 mmol) was then added dropwise and the solution stirred for 0.5 h at −78° C. and a further 5 h at room temperature. Water (10 ml) was then added and products were extracted with ethyl acetate (2×10 ml). Organic extracts were combined, washed with brine (20 ml), dried over anhydrous sodium sulphate, filtered and evaporated to give a yellow oil. Column chromatography (flash silica gel, 5% ethyl acetate in chloroform) gave two diastereoisomers of 1-oxa-6-oxo-2,9-(3,4-dimethoxyphenyl)spiro[4,4]nonane.

A) Major diastereoisomer (Rf 0.2) (118 mg, 28%):
White crystalline solid (crystallised from ethylacetate/DIPE):

m.p. 78–80° C.
analysis calculated for $C_{24}H_{28}O_5$.
Requires C 69.88 H 6.84.
Found C 69.69 H 6.89.
i.r (KBr) 3020, 2980, 1740, 1510, 1420, 1220, 1030 $cm^{-1}$.

$delta_H$(250 MHz, $CDCl_3$) 6.85 (6H, m), 5.23 (1H, dd, J 9.3, 5.9 Hz), 3.89 (3H, s), 3.86 (3H, s), 3.85 (3H, s), 3.69 (3H, s), 3.47(1H, dd, J 12.5, 6.2 Hz), 2.49 (2H, m), 2.13 (3H, m), 1.81 (1H, m), 1.22 (2H, m).

$delta_C$ (62.90 MHz, $CDCl_3$) 207.00, 148.73, 148.10, 133.61, 130.60, 119.73, 118.49, 112.67, 110.88, 110.69, 110.13, 109.67, 108.73, 90.31. 81.74, 55.83, 49.08, 34.51, 32.75, 28.58, 22.11.

Mass spec. [CI, $NH_3$]: 430 ($C_{24}H_{28}O_5.H_2O$), 413 $[M+H]+$.

B) Minor diastereomer ($R_f$ 0.45) (21 mg, 5%): White crystalline solid (crystallised from ethyl acetate/DIPE)

m.p. 128–130° C.
i.r. (CHC13) 2960, 2840, 1740, 1590, 1530, 1450, 1270, 1240, 1140 $cm^{-1}$.

$delta_H$(250 MHz, $CDCl_3$) 6.77 (6H, m), 4.73 (1H, dd, J 10.0, 5.5 Hz), 3.91 (3H, s), 3.84 (3H, s), 3.79 (3H, s), 3.76 (3H, s), 3.01 (1H, dd, J 12.0, 6.3 Hz),2.17 (1H, dd, J 17.2, 7.5 Hz), 2.32 (5H, m), 1.87 (1H, dt, J 10.1, 2.3 Hz), 1.34 (1H, m).

$delta_C$ (62.90 MHz, $CDCl_3$) 148.84, 148.75, 148.40, 148.16, 132.19, 130.38, 121.95, 119.36, 113.07, 110.80, 110.56, 110.11, 109.46, 86.92, 81.21, 55.92, 55.87, 55.75, 51.48, 35.21. 34.51, 27.82, 25.90.

EXAMPLE 2

1-Oxa-6-oxo-7-(3-pyridyl)methylene-2,9-di(3,4-dimethoxyphenyl)spiro[4,4]nonane

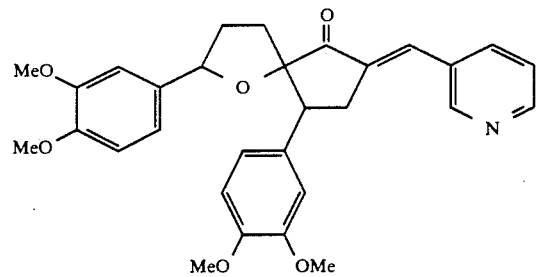

1-Oxa-6-oxo-7-(3-pyridyl)methylene-2,9-di(3,4-dimethoxyphenyl)spiro[4,4]nonane was prepared according to the procedure described in example 1(d) employing 3-pyridine carboxaldehyde in lieu of tert-butyl bromide. Column chromatography (flash silica gel, hexane:ethyl acetate gradient elution 7:3-0:1) provided a yellow oil which was crystallised from ethyl acetate/hexane to give 1-oxa-6-oxo-7-(3-pyridyl)methylene-2,9-di(3,4-dimethoxyphenyl)spiro[4,4]nonane (25% yield).

Pale yellow crystalline solid: m.p. 150° C.
Analysis calculated for $C_{30}H_{31}O_6N$.
Requires C 71.84 H 6.23 N 2.79.

Found C 72.11 H 6.29 N 2.77.

i.r. (KBr) 2920, 2840, 1720, 1510, 1240, 1020 cm$^{-1}$.

delta$_H$ (250 MHz, CDCl$_3$) 8.87 (1H, s), 8.62 (1H, d, J 1.0 Hz), 7.90 (1H, d, J 8.0 Hz), 7.56 (1H, br s) 7.38 (1H, dd, J 8.0, 4.8 Hz), 6.85 (6H, m), 5.25 (1H, dd, J 9.0, 6.1 Hz), 3.87 (3H, s), 3.85 (3H, s), 3.84 (3H, s), 3.70 (3H, s), 3.55 (1H, dd, J 10.2, 7.5 Hz), 3.30 (1H, ddd, J 16.8, 2.2, 2.9 Hz), 3.13 (1H, ddd, J 16.8, 2.2, 2.9 Hz), 2.26 (1H, m), 1.92 (2H, m), 1.44 (1H, m).

delta$_C$ (250 MHz, CDCl$_3$) 206.85, 151.60, 150.13, 148.81, 148.70, 148.56, 148.31, 137.10, 134.82, 133.72, 131.12, 130.53, 123.64, 119.67, 118.57, 112.49, 110.93, 110 88, 110.09, 90.56, 81.84, 55.88, 55.80, 47.56, 33.30, 30.99, 28.71.

Mass spec. [FAB] 501 (M+).

EXAMPLE 3

1-Oxa-6-oxo-7-(2-pyridyl)methylene-2,9-di(3,4-dimethoxyphenyl)spiro[4,4]nonane

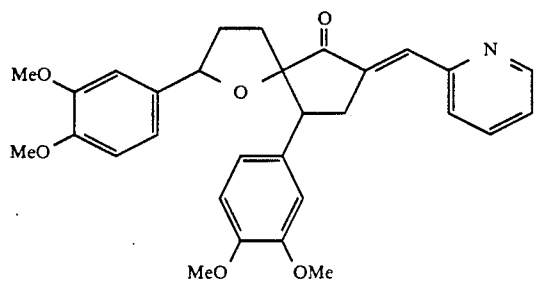

Utilising the procedure described in example 2 employing 2-pyridinecarboxaldehyde in lieu of 3-pyridinecarboxaldehyde gave 1-oxa-6-oxo-7-(2-pyridyl)methylene-2,9-di(3,4-dimethoxyphenyl)spiro[4,4]nonane (13% yield).

Pale yellow crystalline solid: m.p. 143–145° C.

i.r. (CDCl$_3$) 3150, 2980, 2900, 2240, 1815, 1795, 1460, 1380, 1095 cm$^{-1}$.

delta$_H$ (250 MHz, CDCl$_3$) 8.75 (1H, d, J 3.7 Hz), 7.75 (1H, dt, J 7.8, ,1.9 Hz), 7.53 (2H, m), 7.24 (1H, m), 7.01–6.78 (6H, m), 5.30 (1H, dd, J 8.9, 6.1 Hz), 3.90 (3H, s), 3.87 (3H, s), 3.86 (3H, s,), 3.73 (3H, s), 3.56 (1H, dd, J 11.2, 7.3 Hz), 3.24 (2H, ddd, J 17.9, 11 2, 3.2 Hz), 2.22 (1H, m), 1.93 (2H, m), 1.39 (1H, m).

EXAMPLE 4

1-Oxa-6-oxo-7-(4-pyridyl)methylene-2,9-di(3,4-dimethoxyphenyl)spiro[4,4]nonane

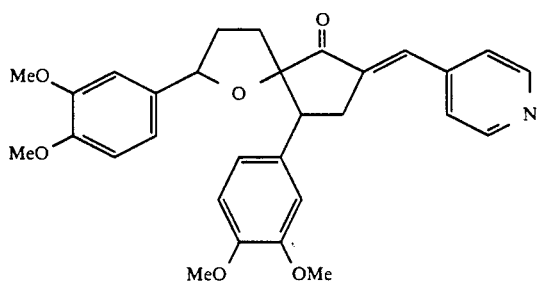

Utilising the procedure described in example 2 employing 4-pyridinecarboxaldehyde in lieu of 3-pyridinecarboxaldehyde gave 1-oxa-6-oxo-7-(4-pyridyl)methylene-2,9-di(3,4-dimethoxyphenyl)spiro[4,4]nonane (3% yield).

Pale yellow viscous oil:

i.r. (CHCl3) 3020, 2970, 2390, 1510, 1415, 925 cm$^{-1}$ delta$_H$ (250 MHz, CDCl$_3$) 8.71 (2H, d, J 5.9 Hz), 7.49 (1H, t, J 2.5 Hz), 7.44 (2H, d, J 6.1 Hz), 6.85 (6H, m), 5.25 (1H, dd, J 8.9, 6.1 Hz), 3.89 (3H, s), 3.88 (3H, s), 3.87 (3H, s), 3.72 (3H, s) 3.57 (1H, dd, J 10.0, 7.4 Hz), 3.36 (1H, ddd, J 17.1, 10.2, 2.9 Hz), 3.13 (1H, ddd, J 17.1, 10.2, 3.0 Hz) 2.27 (1H, m), 1.93 (2H, m), 1.46 (1H, m).

EXAMPLE 5

1-Oxa-6-oxo-7-(3-chlorophenyl)methylene-2,9-di(3,4-dimethoxyphenyl)spiro[4,4]nonane

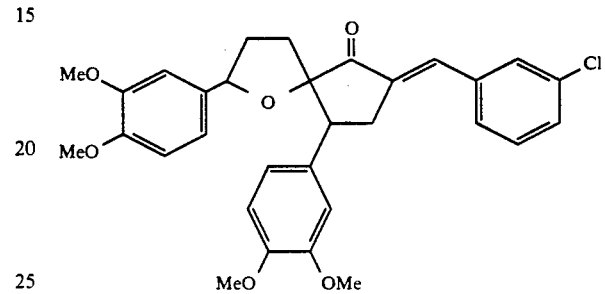

Utilising the procedure described in example 2 employing 3-chlorobenzaldehyde in lieu of 3-pyridinecarboxaldehyde gave 1-oxa-6-oxo-7-(3-chlorophenyl)-methylene-2,9-di (3,4-dimethoxyphenyl)spiro[4,4]nonane (2% yield).

Pale yellow crystalline solid: m.p. 145–147° C.

Analysis calculated for C$_{31}$H$_{31}$O$_6$Cl.

Requires C 69.59 H 5.84 .

Found C 68.72 H 5.84.

i.r. (CDCl3) 3150, 2980, 2240, 1795, 1710, 1465, 1375, 1090 cm$^{-1}$.

delta$_H$ (250 MHz, CDCl$_3$) 7.59 (1H, s), 7.53 (1H, t, J 2.4 Hz), 7.47 (2H, m), 7.38 (1H, d, J 4.2 Hz), 6.86 (6H, m), 5.25 (1H, dd, J 9.0, 6.1 Hz), 3.89 (3H, s), 3.87 (3H, s) 3.86 (3H, s), 3.73 (3H, s,), 3.56 (1H, dd, J 9.9, 7.2 Hz), 3.35 (1H, ddd, J 17.2, 10.4, 3.0 Hz), 3.08 (1H, ddd, J 17.3, 10.4, 3.1 Hz), 2.18 (1H, m), 1.92 (2H, m), 1.45 (1H, m).

EXAMPLE 6

1-Oxa-6-oxo-7-(3,4,5-trimethoxyphenyl)methylene-2,9-di(3,4dimethoxyphenyl)spiro[4,4]nonane

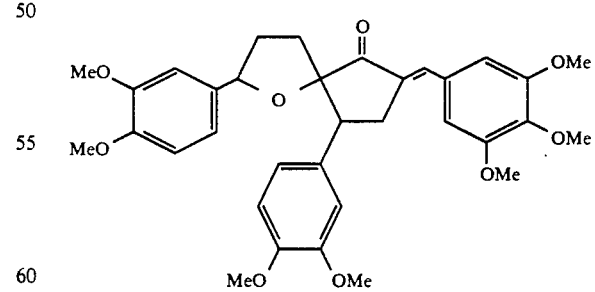

Utilising the procedure described in example 2 employing (3,4,5-trimethoxy)benzaldehyde in lieu of 3-pyridinecarboxaldehyde gave 1-oxa-6-oxo-7-(3,4,5-trimethoxyphenyl)methylene-2,9-di(3,4dimethoxyphenyl)spiro[4,4]nonane (14% yield).

Pale yellow crystalline solid: m.p. 147–148° C.

Analysis calculated for C$_{34}$H$_{38}$O$_9$.

Requires C 69.13 H 6.48.
Found C 68.75 H 6.55.
i.r. (KBr) 3020, 1740, 1510, 1420, 1220, 1030 cm$^{-1}$
delta$_H$(250 MHz, CDCl$_3$) 7.53 (1H, br t), 6.84 (8H, m)
5 23 (1H dd, J 9.0, 6.0 Hz), 3.90 (9H, s), 3.88 (3H, s), 3.86 (3H, s), 3.85 (3H, s), 3.71 (3H, s), 3.39 (1H, ddd, J 16.6, 9.7, 2.5 Hz), 3.08 (1H, ddd, J 16.6, 9.7, 2.5 Hz), 2.25 (1H, m), 1.92 (2H, m), 1.45 (1H, m).

EXAMPLE 7

1-Oxa-6-oxo-7-dimethylmethylene-2,9-di(3,4-dimethoxyphenyl)spiro[4,4]nonane

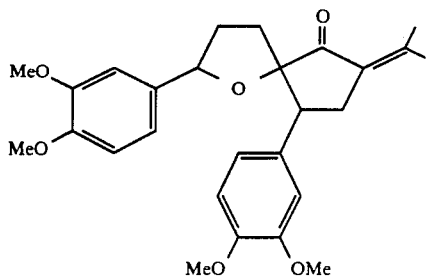

Utilising the procedure described in example 2 employing acetone in lieu of 3-pyridinecarboxaldehyde gave 1-oxa-6-oxo-7-dimethylmethylene-2,9-di(3,4-dimethoxyphenyl) spiro[4,4]nonane (22%).
Colourless oil.
delta$_H$(250 MHz, CDCl$_3$) 6.83 (6H, m), 5.24 (1H, dd, J 9.0, 6.0 Hz), 3.83 (3H, s), 3.82 (3H, s), 3.81 (3H, s), 3.75 (3H,s), 3.83 (1H, dd, J 11.4, 4.0 Hz), 2.95 (1H, m), 2.83 (1H, m), 2.42 (1H, m), 2.31 (3H, s), 2.42 (2H, m), 1.91 (3H, s), 1.28 (1H, m).

EXAMPLE 8

1-Oxa-6-oxo-7-tert-butylmethylene-2,9-di(3,4-dimethoxyphenyl)spiro[4,4]nonane

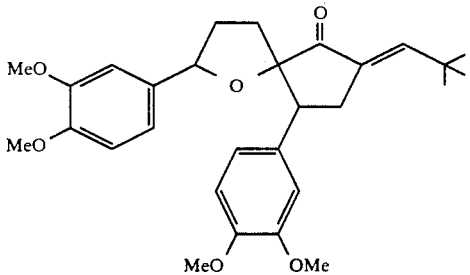

Utilising the procedure described in example 2 employing trimethylacetaldehyde in lieu of 3-pyridinecarboxaldehyde gave 1-oxa-6-oxo-7-tert-butylmethylene-2,9-di(3,4-dimethoxyphenyl)-spiro[4,4]nonane (13% yield).
White crystalline solid: m.p. 134-135° C.
Analysis calculated for C$_{29}$H$_{36}$O$_6$.
Requires C 72.48 H 7.55.
Found C 72.12 H 7.56.
i.r. (KBr) 3020, 1740, 1510, 1420, 1220, 1030 cm$^{-1}$.
delta$_H$(250 MHz, CDCl$_3$) 6.82 (7H, m), 5.20 (1H, dd, J 8.8, 6.1 Hz), 3.87 (3H, s), 3.85 (3H, s), 3.84 (3H, s), 3.69 (3H, s), 3.42 (1H, dd, J 10.4, 7.4 Hz), 3.18 (1H, ddd, J 16.3, 7.5, 2.1 Hz), 2.83 (1H, ddd, J 16.3, 7.5, 2 1 Hz), 2.18 (1H, m), 1 81 (1H, m), 1.42 (1H, m), 1.21 (9H, s).

EXAMPLE 9

1-Oxa-6-oxo-7-heptylmethylene-2,9-di(3,4-dimethoxyphenyl)spiro[4,4]nonane

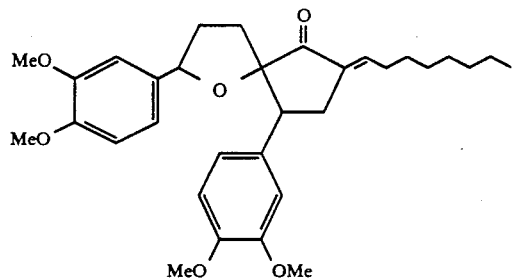

Utilising the procedure described in example 2 employing octan-1al in lieu of 3-pyridinecarboxaldehyde gave 1-oxa-6-oxo-7-heptylmethylene-2,9-di(3,4-dimethoxyphenyl) spiro[4,4]nonane (2% yield).
White crystalline solid: m.p. 78-81° C.
Analysis calculated for C$_{32}$H$_{42}$O$_6$.
Requires C 73.53 H 8.10 .
Found C 73.29 H 8.20.
i.r. (CDCl$_3$) 3150, 2980, 2240, 1795, 1465, 1375, 1090 cm$^{-1}$. delta$_H$(250 MHz, CDCl$_3$) 6.84 (6H, m), 5.25 (1H, dd, J 8.9, 6.0 Hz), 3.89 (3H, s), 3.87 (3H, s), 3.86 (3H, s), 3.71 (3H, s), 3.46 (1H, dd, J 11.0, 7.6 Hz), 2.95 (1H, m), 2.71 (1H, m), 2.23 (2H, m), 1.82 (2H, m), 1.52 (2H, m), 1.30 (10H, br m), 0.89 (3H, t, J 6.8 Hz).

EXAMPLE 10

1-Oxa-6-oxo-7-(3-pyridylethyl)methylene-2,9-di(3,4-dimethoxyphenyl)spiro[4,4]nonane

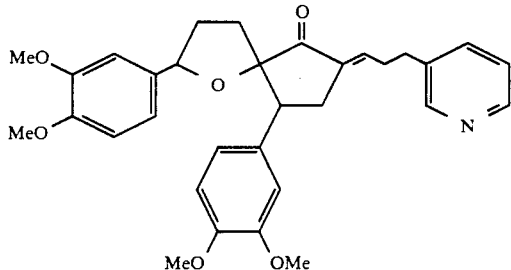

(a) 3-(3-Pyridyl)-1-propanal

A solution of oxalyl chloride (2.55 g, 20.1 mmol) in anhydrous DCM (150 ml) was cooled to −78° C. and dimethylsulphoxide (3.77g, 40.1 mmol) added dropwise with stirring. After two minutes, 3(3-pyridyl)-1-propanol (0.625 g, 3.79 mmol) was added and stirring continued for a further fifteen minutes Triethylamine (12.70 ml, 91.2 mmol) was then added and stirring continued for five minutes before allowing the solution to warm to room temperature. Water (150 ml) was added the organic layer separated and the aqueous layer extracted with DCM (2×100 ml). The organic extracts were combined, washed with brine (50 ml), dried over anhydrous magnesium sulphate, filtered and evaporated to give a yellow oil (2.20 g, 90%) which was used directly in the next step.
delta$_H$ (250 MHz, CDCl$_3$) 9.61 (1H, s), 8.29 (1H, s), 8.25 (1H, d), 7.35 (1H, d), 7.03 (1H, dd), 2.75 (2H, t), 2.63 (2H, t).

(b) 1-Oxa-6-oxo-7-(3-pyridylethyl)methylene-2,9-di(3,4-dimethoxyphenyl)spiro[4,4]nonane Utilising the procedure described in example 2 employing 3-(3-pyridyl)-1-propanal in lieu of 3-pyridinecarboxaldehyde gave 1-oxa-6-oxo-7-(3-pyridylethyl)methylene-2,9-di (3,4-dimethoxyphenyl)-spiro [4,4]nonane (1% yield).

Viscous oil:
i.r. (CDCl3) 3150, 2980, 2240, 1795, 1465, 1380, 1090 cm$^{-1}$.

delta$_H$(250 MHz, CDCl3) 8.46 (2H, br s), 7.49 (1H, d, J 7.8 Hz), 7.22 (1H, m) 6.89–6.76 (7H, br m), 5.24 (1H, dd, J 9.0, 6.1 Hz), 3.89 (3H, s), 3.87 (3H, s), 3.85 (3H, s), 3.70 (3H, s), 3.39 (1H, dd, J 11.0, 7.5 Hz), 2.80 (2H, br m), 2.68–1.19 (8H, br m).

EXAMPLE 11

1-Oxa-6-oxo-7-(3-pyridylbutyl)methylene-2,9-di(3,4-dimethoxyphenyl)spiro[4,4]nonane

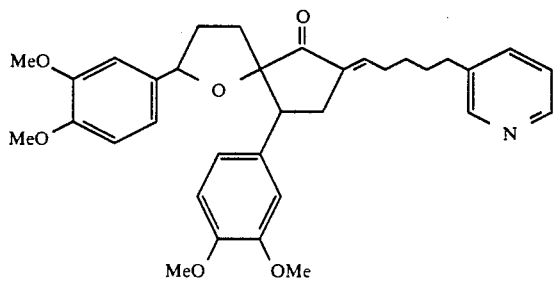

(a) 5-(3-pyridyl)-1-pent-4-ynol

To a stirred solution of 3-bromopyridine (4.09 g, 26 mmol), 4-pentyn-1-ol (2.58 g, 31 mmol) and triethylamine (12 ml) in anhydrous DCM (20 ml) was added bis(-triphenylphosphine)-palladium dichloride (0.05 g, 0.07 mmol) and copper(I) iodide (0.05 g, 0.26 mmol). The mixture was refluxed for 20 h under argon. After cooling, water (20 ml) was added and the products extracted into DCM. The combined organic extracts were washed with saturated potassium carbonate (50 ml) dried over anhydrous magnesium sulphate, filtered and evaporated to provide a brown oil. Column chromatography (flash silica gel, ethyl acetate) gave 5-(3-pyridyl)-1-pent-4-ynol (0.37 g, 7%) as a colourless oil.

delta$_H$ (250 MHz, CDCl3) 8.61 (1H, d), 8.45 (1H, d), 7.66 (1H, dt), 7.21 (1H, dd), 3.80 (2H, t), 2.56 (2H, t), 2.39 (1H, br s), 1.87 (2H, m).

(b) 5-(3-Pyridyl)-1-pentanol 5-(3-Pyridyl)-1-pentyn-4-ol (0.776 g, 4.82 mmol) was added to a stirred suspension of 10% palladium on charcoal (0.2 g) in methanol (30 ml). The reaction was stirred at room temperature under a hydrogen atmosphere for 48 h, by which time hydrogen uptake had ceased. The mixture was filtered through celite and evaporated to provide a yellow oil. Column chromatography (flash silica gel, 5% methanol in ethyl acetate) gave 5-(3-pyridyl)-1-pentanol (0.769 g, 97%) as a colourless oil.

delta$_H$(250 MHz, CDCl3) 8.25 (2H, m), 7.38 (1H, d, J 7.8 Hz), 7.09 (1H, m), 4.36 (1H, br s), 3.52 (2H, t), 2.48 (2H t), 1.50 (4H, br m), 1.33 (2H, br m).

(c) 5-(3-Pyridyl)-1-pentanal

Utilising the procedure described in example 10(a) employing 5-(3-pyridyl)-1-pentanol in lieu of 3-(3-pyridyl)-1-propanol gave after purification by column chromatography (flash silica gel, 5% methanol in chloroform) 5-(3-pyridyl)-1-pentanal (96% yield).

Colourless oil.

delta$_H$(250 MHz, CDCl3) 9.67 (1H, t), 8.34 (2H, br s), 7.41 (1H, d, J 7.8 Hz), 7.14 (1H, m), 2.58 (2H, quartet), 2.39 (2H, m), 1.59 (4H, m).

(d) 1-Oxo-6oxo-7-(3-pyridylbutyl)methylene-2,9-di(3,4-dimethoxyphenyl) spiro[4,4]nonane Utilising the procedure described in example 2 employing 5-(3-pyridyl)-1-pentanal in lieu of 3-pyridinecarboxaldehyde gave 1-oxa-6-oxo-7-(3-pyridylbutyl)methylene-2,9-di (3,4-dimethoxyphenyl)spiro[4,4]nonane (2% yield).

Pale yellow crystalline solid: m.p. 105–108° C.
Analysis calculated for C34H39NO6.
Requires C 73.23 H 7.05 N 2.51.
Found C 72.77 H 7.11 N 2.49.
i.r. (CDCl3) 3150, 3020, 2240, 1795, 1465, 1375, 1215, 1090 cm$^{-1}$.

delta$_H$(250 MHz, CDCl3) 8.46 (2H, br s), 7.49 (1H, d, J 7.8 Hz), 7.22 (1H, m), 6.84 (7H, m), 5.24 (1H, dd, J 9.0, 6.1 Hz), 3.89 (3H, s), 3.87 (3H, s), 3.85 (3H, s), 3.70 (3H, s), 3.46 (1H, dd, J 11.0, 7.5 Hz), 2.93 (1H, m), 2.65 (2H, t, J 7.1 Hz), 2.25 (3H, m), 1.86–1.54 (8H, br m).

EXAMPLE 12

1-Oxa-6-oxo-7-(3-pyrrolyl)methylene-2,9-di(3,4-dimethoxyphenyl)spiro[4,4]nonane

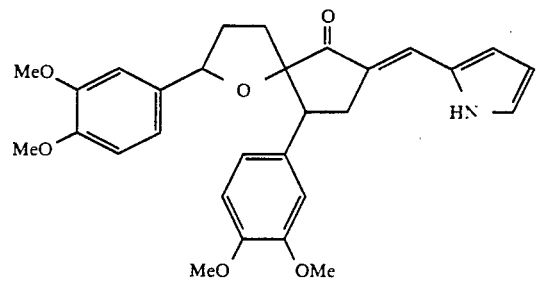

1-Oxa-6-oxo-7-(3-pyrrolyl)methylene-2,9-di(3,4-dimethoxyphenyl)-spiro[4,4]nonane was prepared according to the procedure outlined in example 2 employing pyrrole-2-carboxaldehyde in lieu of 3-pyridinecarboxaldehyde. Column chromatography (flash silica gel, chloroform:ethyl acetate (3:2)) provided a yellow oil which was crystallised from ethyl acetate/hexane to give 1-oxa-6-oxo-7-(3-pyrrolyl)methylene-2,9-di (3,4-dimethoxyphenyl)-spiro[4,4]nonane (1.5% yield).

Yellow crystalline solid: m.p. 172–173° C.
Analysis calculated for C29H31NO6.0.3H2O.
Requires C 70.37 H 6.44 N 2.83,
Found C 70.44 H 6.44 N 2.82.
i.r. (CHCl3) 3690, 3480, 2960, 2840, 1740, 1680, 1560, 1340 cm$^{-1}$.

delta$_H$(250 mHz, CDCl3) 7.08 (1H, s), 6.98–6.80 (6H, br m), 6.59 (1H, br m), 6.35 (1H, br m), 5 32, (1H, dd, J 9.3, 5.9 Hz), 3.92 (3H, s), 3.89 (3H, s), 3.87 (3H, s), 3.65 (3H, s), 3.60 (1H, dd, J 12.3, 6.1 Hz), 3.05 (1H, m), 2.90

(1H, m), 2.18 (1H, m), 1.97 (2H, m), 1.62 (1H, m), 1.28 (2H, m).

EXAMPLE 13

1-Oxa-6-oxo-7-benzoyl-2,9-di(3,4-dimethoxyphenyl)-spiro-[4,4]nonane

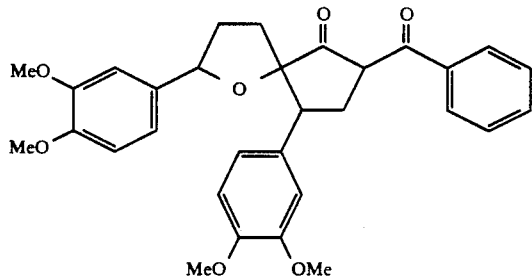

Using the procedure described in example 2 employing benzoyl chloride in lieu of 3-pyridinecarboxaldehyde gave 1-oxa-6-oxo-7-benzoyl-2,9-di (3,4-dimethoxyphenyl)spiro[4,4]nonane (12% yield.

Pale yellow crystalline solid: m.p. 132–135° C.
Analysis calculated for $C_{31}H_{32}O_7$.
Requires C 72.08 H 6.24,
Found C 72.69 H 6.61.

$delta_H$ (250 MHz, $CDCl_3$) 7.85 (1H, m), 7.65 (1H, m), 7.47 (3H, m), 6.87 (6H, m), 5.28 (1H, dd, J 9.0, 6.3 Hz), 3.89 (3H, s), 3.87 (3H, s), 3.86 (3H, s) 3.72 (3H, s), 3.56 (1H, dd, J 11.0, 7.3 Hz), 3.37 (1H, ddd, J 16.7, 7.7, 2.8 Hz) 3.11 (1H, ddd, J 14.2, 10.2, 2.8 Hz), 2.24 (1H, m), 1.97 (2H, m), 1.50 (2H, m).

EXAMPLE 14

1-Oxa-6-oxo-7-(2-pyridyl)methyl-2,9-di(3,4-dimethoxyphenyl)spiro[4,4]nonane

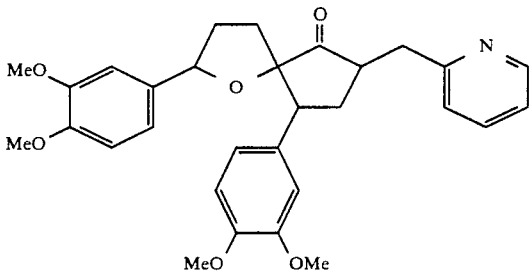

a) Sodium Hydrogen Telluride

A mixture of tellurium (97 mg, 0.6 mmol) and sodium borohydride (60 mg, 1 5 mmol) in deoxygenated ethanol (5 ml) were heated together at reflux for 1h then allowed to cool to room temperature before use.

b) 1-Oxa-6-oxo-7-(2-pyridyl)methyl-2,9-di(3,4-dimethoxyphenyl)spiro[4,4]nonane

A solution of 1-oxa-6-oxo-7-(2-pyridyl)methylene-2,9-di(3,4dimethoxyphenyl)spiro[4,4]nonane (60mg, 0.12 mmol) in ethanol (5 ml) was added to a solution of sodium hydrogen telluride (3 ml as prepared above) and the mixture allowed to stir at 40° C. for 1 h then at room temperature for a further 1 h. Saturated ammonium chloride solution (5 ml) was then added and ethanol removed under reduced pressure. The residue was partitioned between DCM (15 ml) and water (10 ml), layers separated and the aqueous layer further extracted with DCM (2×5ml). The combined organic layers were dried over anhydrous sodium sulphate and evaporated. Column chromatography (flash silica gel; ethyl acetate) followed by crystallisation from ethyl acetate/hexane gave 1-oxa-6-oxo-7-(2-pyridyl)methyl-2,9-di(3,4-dimethoxyphenyl)spiro[4,4]nonane (30mg, 50%).

White crystalline solid: m.p. 80–82° C.
Analysis calculated for $C_{30}H_{33}NO_6$.
Requires C 71.55 H 6.60 N 2.78.
Found C 71.30 H 6.65 N 2.72.
i.r. ($CHCl_3$) 2940, 1740, 1590, 1460, 1250, 1020 $cm^{-1}$.
$delta_H$ (250MHz, $CDCl_3$) 8.50 (2H, d, J 5.9 Hz), 7.59 (1H, m), 7.25 (1H, dd, J 7.4, 4.8 Hz), 6.80, (6H, m), 5.23 (1H, dd, J 9.4, 5.8 Hz), 3.86, 3.85, 3.84, 3.64 (12H, 4s), 3.66 (1H, dd, J 7.6, 5.6 Hz), 3.20 (1H, dd), 2.79 (2H, m), 2.22 (1H, m), 2.05 (1H, m), 1.78 (1H, m), 1.24 (1H, m).

$delta_C$ (250 MHz, $CDCl_3$) 219.56, 150.36, 148.39, 148.00, 136.52, 134.34, 133.33, 129.85, 123.37, 119.62, 118.46, 112.60, 110.85, 110.56, 110.10, 90.27, 81.96, 55.84, 55.67, 47.94, 47.66, 46.52, 34.20, 32.92, 28.82, 27.83, 27.28.

Mass spectra [C.I. $NH_3$]504 [M+H]+

EXAMPLE 15

1-Oxa-6-hydroxy-2,9-di(3,4-dimethoxyphenyl)-spiro[4,4]nonane

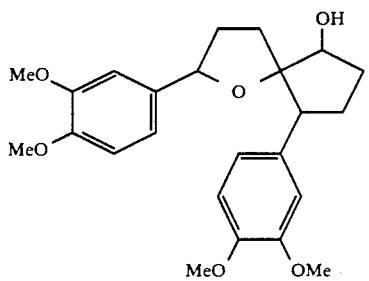

To a stirred solution of 1-oxa-6-oxo-2,9-(3,4-dimethoxyphenyl)spiro[4,4]nonane (250 mg, 0.6 mmol) in ethanol (5) at room temperature, was added sodium borohydride (40 mg, 2.5 mmol) and the mixture allowed to stir at room temperature over night. Water (10 ml) was then added and products extracted with DCM (2×10 ml). Organic extracts were combined, washed with water (10 ml), brine (10 ml), dried over anhydrous sodium sulphate and evaporated. Column chromatography (flash silica gel, DCM : diethyl ether (9:1)) gave 1-oxa-6-hydroxy-2,9-di(3,4-dimethoxyphenyl)spiro[4,4]nonane (115 mg, 46%).

Colourless oil.
Analysis calculated for $C_{24}H_{30}O_6$.
Requires C 66.54 H 7.29.
Found C 66.50 H 7.20.

$delta_H$ (250 MHz, $CDCl_3$) 6.82 (6H, m), 4.77 (1H, dd, J 9.3, 5.9 Hz), 3.90 (1H, m), 3.86 (3H, s), 3.85 (3H, s), 3.83 (3H, s), 3.73 (3H, s), 3.52 (1H, t, J 9.5 Hz), 2.05 (3H, m), 1.85 (3H, m), 1.58 (1H, m), 1.29 (1H, m).

$delta_C$ (250 MHz, $CDCl_3$) 148.78, 148.48, 148.20, 147.59, 133.89, 132.25, 120.23, 112 87, 110.84, 110.52, 109.68, 93.03, 80.37, 76.81, 55.78 55.65, 48.01 33.98, 30.24, 28.95, 24.63, 22.72.

EXAMPLE 16

1-Oxa-6-(3,5-dinitro)benzoyloxy-2,9-di(3,4-dimethoxyphenyl)spiro[4,4]nonane

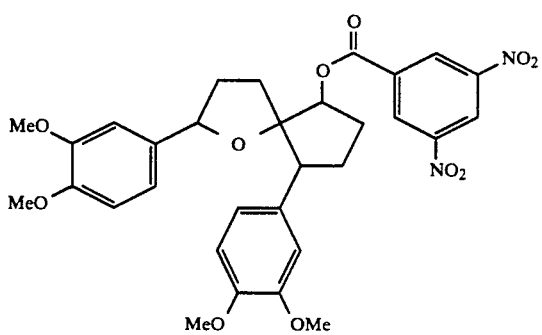

To a solution of 2-oxa-6-hydroxy-2,9-(3,4-dimethoxyphenyl)-spiro[4,4]nonane (120 mg, 0.29 mmol in DCM (3 ml) was added triethylamine (1 ml, 1.38 mmol), dimethylaminopyridine (51 mg, 0.42 mmol) and 3,5-dinitrobenzoyl chloride (92 mg, 0.4 mmol) and the resulting solution allowed to stir at room temperature for 4h. DCM (15 ml) was added and the solution washed with water (2×10ml), dried over anhydrous sodium sulphate and evaporated. Column chromatography (flash silica gel, DCM:diethyl ether (9:1)) provided a yellow oil which was crystallised from ethyl acetate/hexane to give 1-oxa-6-(3,5-dinitro)benzoyloxy-2,9-di(3,4-dimethoxyphenyl)spiro[4,4]nonane (70 mg, 40%).

Yellow crystalline solid: m.p. 82–84° C.
Analysis calculated for $C_{31}H_{22}N_2O_{11}$.
Requires C 61.18 H 5.30 N 4.60.
Found C 61.04 H 5.42 N 4.67.
i.r. (KBr) 2960, 1760, 1550, 1340, 1270, 1020 cm$^{-1}$.
delta$_H$(250 MHz, CDCl$_3$) 9.22 (2H, br s), 7.29 (1H, s), 6.74 (6H, br m), 5.84 (1H, m), 4.81 (1H, dd, J 9.0, 6.2 Hz), 3.89 (3H, s), 3.81 (3H, s), 3.74 (3H, s), 3.71 (3H, s), 3.56 (1H, m), 2.15 (1H, m), 1.75 (1H, m), 1.32 (1H, m).

EXAMPLE 17

1-Oxa-6-cyanomethylene-2,9-di(3,4-dimethoxyphenyl)-spiro[4,4]nonane

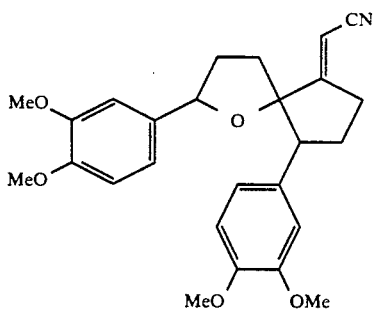

A solution of lithium diisopropylamide (1.5 M, 2.43 ml, 3.64 mmol) in THF was added dropwise to a solution of dry acetonitrile (0.2 ml, 3.64 mmol) in THF (5 ml) at −78° C. After stirring for 10 min. at −78° C., a solution of 1-oxa-6-oxo-2,9-(3,4-dimethoxyphenyl)spiro[4,4nonane (0.75 g, 1.82 mmol) in THF (10 ml) was added dropwise. After stirring for 0.5 h at −78° C., the solution was allowed to warm to 0° C. and stirred for a further 2 h. The reaction was quenched by addition of brine (10 ml) at 0° C., and was then allowed to warm to room temperature. The mixture was partitioned between water (10 ml) and ethyl acetate (10 ml). The aqueous layer was extracted with ethyl acetate (2×10 ml) and the organic layers combined, washed with brine (2×10 ml), dried over anhydrous sodium sulphate and evaporated. Column chromatography (Flash silica gel; 10% ethyl acetate in DCM) gave 1-oxa-6-cyanomethylene-2,9-di(3,4dimethoxyphenyl)spiro[4,4]nonane (450 mg, 55%).

White crystalline solid: m.p. 140–141° C.
Analysis calculated for $C_{26}H_{29}NO_5.0.2H_2O$.
Requires C 71.12 H 6.75 N 3.19.
Found C 71.14 H 6.75 N 3.09.
i.r. (KBr) 2940, 2210, 1590, 1510, 1250, 1025 cm$^{-1}$.
delta$_H$ (250 MHz, CDCl$_3$) 6.81 (6H, m), 6.06 (0.5H, brs), 5.56 (0.5H, t, J 2.6 Hz), 4.99 (0.5H, dd, J 9.8, 5.4 Hz), 4.86 (0.5H, dd, J 4.8, 10.9 Hz), 3.91, 3.87, 3.86 (9H, 3s), 3.59, 3.51 (3H, 2s), 3.30 (1H, m), 2.82 (1H, m), 2.65 (1H, m), 1.92 (4H, br m), 1.05 (1H, m).

EXAMPLE 18

1-Oxa-6-oxo-2,9-di(4-methoxyphenyl)spiro[4,4]nonane

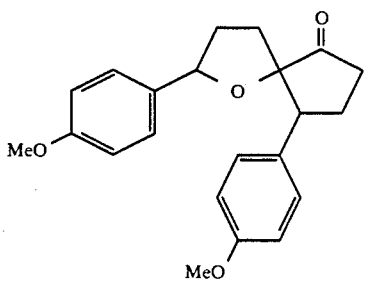

(a) 2-(4-Methoxyphenyl)-5-methoxytetrahydrofuran

Utilising the procedure described in example 1(b) employing 4-bromoanisole in lieu of 4-bromoveratole gave 2-(4-methoxyphenyl)-5-methoxytetrahydrofuran (81% yield).

Colourless oil.
delta$_H$ (250 MHz, CDCl$_3$) 7.33 (2H, d), 6.90 (2H, d), 5.25 (0.5H, dd), 5.10–4.95 (1.5H, m), 3.79 (3H, s), 3.45, 3.43 (2H, 2s), 2.45–1.68 (4H, m).

(b) 2-Benzenesulphonyl-5-(4-methoxyphenyl)tetrahydrofuran

Utilising the procedure described in example 1(c) employing 2-(4-methoxyphenyl)-5-methoxytetrahydrofuran in lieu of 2-(3,4-dimethoxyphenyl)-5-methoxytetrahydrofuran gave 2-benzene-sulphonyl-5-(4-methoxyphenyl)tetrahydrofuran (33%).

White crystalline solid.
delta$_H$ (250 MHz, CDCl$_3$) 7.96 (2H, m), 7.73–7.44 (4H, m), 7.23 (1H, d), 6.90 (2H, m), 5.35 (0.5H, dd), 5.15 (0.5H, dd), 4.99 (1H, dd), 3.85, 3.80 (3H, 2s), 3.03-2.83 (4H, m).

(c) 1-Oxa-6-oxo-2,9-di(4-methoxyphenyl)spiro[4,4]nonane

Utilising the procedure described in example 1(d) employing 2-benzenesulphonyl-5-(4-methoxyphenyl)-tetrahydrofuran in lieu of 2-benzenesulphonyl-5-(3,4-dimethoxyphenyl)tetrahydrofuran gave 1-oxa-6-oxo-2,9-di(4-methoxyphenyl)spiro[4,4]nonane (3% yield).

Colourless viscous oil:

i.r. (CHCl$_3$) 3030, 2390, 1510, 1420, 1230, 1190, 920 cm$^{-1}$.

delta$_H$ (250 MHz, CDCl$_3$) 7.29 (2H, d, J 9.4 Hz), 7.20 (2H, d, J 8.7 Hz), 6.91 (2H, d, J 8.7 Hz), 6.84 (2H, d, J 8.7 Hz), 5.19 (1H, dd, J 9.4, 5.6 Hz), 3.84 (3H, s), 3.81 (3H, s), 3.48 (1H, dd, 12.4, 6.4 Hz), 2.49 (1H, m), 2.18 (3H, m), 1.79 (2H, m), 1.24 (2H, m).

EXAMPLE 19

1-Oxa-6-oxo-7-(3-pyridyl)methylene-2,9-di(4-methoxyphenyl)spiro[4,4]nonane

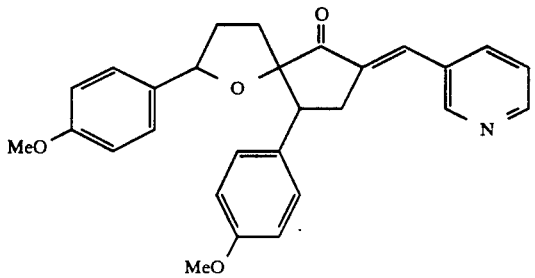

Utilising the procedure described in example 2 employing 2-benzenesulphonyl-5-(4-methoxyphenyl)tetrahydrofuran in lieu of 2-benzenesulphonyl-5-(3,4-dimethoxyphenyl)tetrahydrofuran gave 1-oxa-6-oxo-7-(3-pyridyl)methylene-2,9-di(4-methoxyphenyl)spiro[4,4-]nonane (7% yield).

Pale yellow crystalline solid: m.p. 109–112° C.
Analysis calculated for C$_{28}$H$_{27}$NO$_4$.0.1H$_2$O.
Requires C 76.17 H 6.16 N 3.17.
Found C 75.80 H 6.30 N 3.11.

delta$_H$ (250 MHz, CDCl$_3$) 8.85 (1H, s), 8.60 (1H, d, J 1.0 Hz), 7.90 (1H, d, J 8.0 Hz), 7.60 (1H, s), 7.35 (1H, dd, J 8.0, 4.8 Hz), 7.25, 6.85 (8H, 2m), 5.21 (1H, dd, J 9.0, 6.1 Hz), 3.82 (3H, s), 3.80 (3H, s), 3.60 (1H, dd, J 10.2, 7.5 Hz), 3.36 (1H, ddd, J 16.8, 2.9, 2.2 Hz), 3.10 (1H, ddd, J 16.8, 2.9, 2.2 Hz), 2.26 (1H, m), 1.95 (2H, m), 1.45 (1H, m).

Pharmacology Example 1

The inhibition of $^3$H-PAF binding to human platelet plasma membrane by compounds of general formula I was determined by isotopic labelling and filtration techniques. Platelet concentrates were obtained from a hospital blood bank. These platelet concentrates (500–2500 ml.) were centrifuged at 800 rpm for 10 minutes in a SORVALL RC3B centrifuge to remove the red blood cells present. (The word SORVALL is a trade mark.) The supernatant was subsequently centrifuged at 3,000 rpm in a SORVALL RC3B centrifuge to pellet the platelets present. The platelet rich pellets were resuspended in a minimum volume of buffer (150 mM NaCl, 10 mM Tris, 2 mM EDTA, pH 7.5) and layered onto Ficoll-Paque gradients, 9 ml platelet concentrate to 2 ml Ficoll, and centrifuged at 1,900 rpm for 15 minutes in a SORVALL RT6000 centrifuge. This step removes the residual red blood cells and other nonspecific material such as lymphocytes from the preparation. The platelets which form a band between the plasma and the Ficoll were removed, resuspended in the above buffer and centrifuged at 3,000 rpm for 10 minutes in a SORVALL RT6000 centrifuge. The pelleted platelets were resuspended in buffer (10 mM Tris, 5mM MgCl$_2$, 2 mM EDTA, pH 7.0), snap freezed in liquid N$_2$ and allowed to thaw slowly at room temperature in order to lyse the platelets. The latter step was repeated at least 3 times to ensure proper lysis. The lysed platelets were centrifuged at 3,000 rpm for 10 minutes in a SORVALL RT6000 centrifuge and resuspended in buffer. The latter step was repeated twice in order to remove any cytoplasmic proteins which may hydrolyse the platelet activating factor (PAF) receptor. The prepared platelet membranes may be stored at −70° C. After thawing the prepared membranes were centrifuged in a SORVALL RT6000 at 3,000 rpm for 10 minutes and resuspended in assay buffer.

The assay was conducted by preparing a series of Tris-buffered solutions of the selected antagonist of predetermined concentrations. Each of these solutions contained $^3$H-PAF (0.5 nM; 1-O-[$^3$H]octadecyl-2-acetyl-sn-glycero-3-phosphoryl choline with a specific activity of 132 Ci/mmol), unlabelled PAF (1000 nM), a known amount of the test antagonist, and a sufficient amount of Tris-buffer solution (10mM Tris, 5mM MgCl$_2$, pH 7.0, 0.25% BSA) to make the final volume 1ml. Incubation was initiated by the addition of 100 μg of the isolated membrane fraction to each of the above solutions at 0° C. Two control samples, one (C1) which contained all the ingredients described above except the antagonist and the other (C2) contains C1 plus a 1000-fold excess of unlabelled PAF, were also prepared and incubated simultaneously with the test samples. After 1 hour incubation, each solution was filtered rapidly under vacuo through a WHATMAN GF/C glass fibre filter in order to separate unbound PAF from bound PAF. (The word WHATMAN is a trade mark.) The residue in each case was rapidly washed 4 times with 5 ml cold (4° C.) Tris-buffer solution. Each washed residue was dried under vacuum on a sampling manifold and placed into vials containing 20 ml of OPTIPHASE MP scintillation fluid and the radioactivity counted in a liquid scintillation counter. (The word OPTIPHASE is a trade mark.) Defining the counts for total binding with antagonist from a test sample as "TBA"; the counts for total binding from the control sample C1 as "TB"; and the counts for nonspecific binding from the control sample C2 as "NSB", the percent inhibition of each test antagonist can be determined by the following equation:

$$\%\text{Inhibition} = [(TB-TBA)/SB] \times 100$$

where the specific binding SB=TB-NSB

Table 1 lists results from this assay for inhibition of $^3$H-PAF receptor binding for illustrative examples of the compounds of this invention.

TABLE 1

| Results for inhibition of $^3$H-PAF receptor binding | |
|---|---|
| Example | IC$_{50}$ μM |
| 1A | 12.0 |
| 2 | 3.0 |
| 5 | 5.0 |
| 10 | 1.5 |
| 11 | 1.0 |
| 17 | 1.5 |
| 18 | 5.0 |
| 19 | 9.0 |

Pharmacology Example 2

The activity of the compounds of general formula I is also demonstrated in vivo by their ability to reverse the hypotension caused by an infusion of PAF in rats. Male Sprague-Dawley rats (300-350 gms) were anaesthetised with a mixture of sodium pentobarbitone, 22.5 mg.kg$^{-1}$ and thiopental 62.5 mg.kg$^{-1}$. Through a midline incision in the neck, the trachea was cannulated and the animals breathed spontaneously. A carotid artery was cannulated for the measurement of blood pressure and this signal was used to trigger a rate meter to measure heart rate. Both jugular veins were cannulated: one for the infusion of PAF and the other for the bolus administration of test compounds.

( PAF, 100 ng.kg$^{-1}$ min$^{-1}$ was infused i.v. until a sustained fall in mean blood pressure of 50 mmHg was achieved. Test compounds were administered i.v. as a bolus and resulted in a dose dependent reversal of the PAF induced hypotension. The peak of this reversal was measured and the dose to cause a 50% reversal of the hypotensive PAF response (ED$_{50}$) calculated by straight line interpolation and the results are presented in Table 2.

Table 2: Results for inhibition of PAF-induced hypotension in the rat

| Example | ED$_{50}$ (µg/kg i.v.) |
|---------|------------------------|
| 2       | 800                    |

What is claimed is:

1. A compound of general formula I:

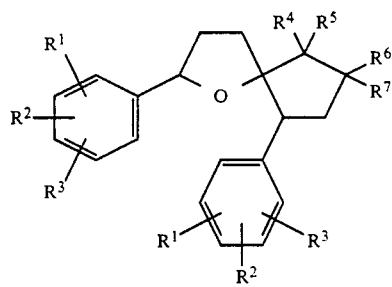

wherein:
each of $R^1$, $R^2$, and $R^3$ independently represents hydrogen, $C_1$-$C_6$ alkyl, $C_2$-$C_6$ alkenyl, $C_1$-$C_6$ alkoxy, $C_1$-$C_6$ thioalkyl, halo, CN, NO$_2$, SOC$_1$-$C_6$ alkyl, SO$_2$C$_1$-$C_6$ alkyl, SO$_2$NH$_2$, COC$_1$-$C_6$ alkyl, CHO, COOC$_1$-$C_6$ alkyl, CH$_2$OH, benzyl, benzoyl, CF$_3$, CONH$_2$, NHCOC$_1$-$C_6$ alkyl;

each of $R^4$ and $R^5$ independently represents hydrogen, $C_1$-$C_6$ alkyl, $C_2$-$C_6$ alkenyl, $C_1$-$C_6$ alkoxy, $C_1$-$C_6$ thioalkyl, halo, CN, NO$_2$, SOC$_1$-$C_6$ alkyl, SO$_2$C$_1$-$C_6$ alkyl, SO$_2$NH$_2$, COOH, COC$_1$-$C_6$ alkyl, CHO, COOC$_1$-$C_6$ alkyl, CH$_2$OH, OH, benzyl, benzoyl, CF$_3$, CONH$_2$, NHCOC$_1$-$C_6$ alkyl or a OC(=O)R$^8$ group wherein R$^8$ represents $C_1$-$C_6$ alkyl, $C_2$-$C_6$ alkenyl, $C_1$-$C_6$ alkoxy, $C_1$-$C_6$ thioalkyl, COC$_1$-$C_6$ alkyl, COOC$_1$-$C_6$ alkyl, benzyl, benzoyl, nitrile, CF$_3$ or a V group wherein V represents a group

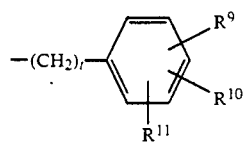

wherein t is an integer from 0 to 3 and each of $R^9$, $R^{10}$ and $R^{11}$ is independently hydrogen, $C_1$-$C_6$ alkyl, $C_2$-$C_6$ alkenyl, $C_1$-$C_6$ alkoxy, $C_1$-$C_6$ thioalkyl, halo, CN, NO$_2$, SOC$_1$-$C_6$ alkyl, SO$_2$C$_1$-$C_6$ alkoxy, SO$_2$NH$_2$, COOH, COC$_1$-$C_6$ alkyl, CHO, COOC$_1$-$C_6$ alkyl, CH$_2$OH, OH, benzyl, benzoyl, CF$_3$, CONH$_2$, NHCOC$_1$-$C_6$ alkyl;

or $R^4$ together with $R^5$ forms a =O, =N-OH, —NHR$^8$ or =CHR$^8$ group, wherein R$^8$ is as defined above;

each of $R^6$ and $R^7$ independently represents hydrogen, $C_1$-$C_6$ alkyl, COC$_1$-$C_6$ alkyl, benzyl, a group V as defined above or a COV group wherein V is as defined above;

or $R^6$ together with $R^7$ form a =CR$^{12}$R$^{13}$ group wherein each of $R^{12}$ and $R^{13}$ independently represent a hydrogen atom, a $C_1$-$C_{18}$ alkyl, a $C_2$-$C_6$ alkenyl or a group V as defined above;

or a pharmaceutically or veterinarily acceptable acid addition salt or hydrate thereof.

2. A compound as claimed in claim 1, in which $R^1$ represents a $C_1$-$C_6$ alkoxy group.

3. A compound as claimed in claim 1, wherein $R^2$ represents a hydrogen atom or a $C_1$-$C_6$ alkoxy group.

4. A compound as claimed in claim 1, wherein $R^3$ represents a hydrogen atom.

5. A compound as claimed in claim 1, wherein $R^7$ represents a hydrogen atom or together with $R^6$ forms =CR$^{12}$R$^{13}$ group; and wherein $R^{12}$ and $R^{13}$ are as defined in claim 1.

6. A compound as claimed in claim 1 wherein $R^4$ represents a hydroxyl group, a OC(=O)R$^8$ group or together with $R^5$ forms a =O or =CHR$^8$ group; wherein $R^8$ is as defined in claim 1.

7. A compound as claimed in claim 1 wherein $R^5$ represents a hydrogen atom or together with $R^4$ forms a =O or =CHR$^8$ group; and wherein $R^8$ is as defined in claim 1.

8. A compound as claimed in claim 1 wherein $R^6$ represents a hydrogen atom, a group V, a group COV or together with $R^7$ forms =CR$^{12}$R$^{13}$ group; and wherein V, $R^{12}$ and $R^{13}$ are as defined in claim 1.

9. A compound as claimed in claim 1 wherein $R^8$ represents a nitrile group or a group V; and wherein V is as defined in claim 1.

10. A compound as claimed in claim 1 wherein V represents a

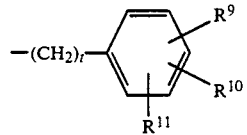

group and t represents an integer of 0 or 1, and wherein $R^9$, $R^{10}$ and $R^{11}$ are as defined in claim 1.

11. A compound as claimed in claim 10, wherein $R^9$ represents a hydrogen atom, a $C_1$-$C_6$ alkoxy group, a halogen atom or a nitro group.

12. A compound as claimed in claim 10, wherein $R^{10}$ represents a hydrogen atom, a $C_1$-$C_6$ alkoxy group or a nitro group.

13. A compound as claimed in claim 10, wherein $R^{11}$ represents a hydrogen atom or a $C_1$-$C_6$ alkoxy group.

14. A compound as claimed in claim 1 wherein $R^{12}$ represents a $C_1$-$C_{18}$ alkyl group, or a group V, wherein V is a defined in claim 1.

15. A compound as claimed in claim 1, wherein $R^{13}$ represents a hydrogen atom or a $C_1$–$C_{18}$ group.

16. 1-Oxa-6-oxo-2,9-di(3,4-dimethoxyphenyl)-spiro[4,4]nonane,
- 1-Oxa-6-oxo-7-tert-butylmethylene-2,9-di(3,4-dimethoxyphenyl)spiro[4,4]nonane,
- 1-Oxa-6-oxo-7-heptylmethylene-2,9-di(3,4-dimethoxyphenyl)-spiro[4,4]nonane,
- 1-Oxa-6-oxo-2,9-di(4-methoxyphenyl)spiro[4,4]nonane, or a salt of such a compound.

17. 1-Oxa-6-oxo-7-(3-chlorophenyl)methylene-2,9-di(3,4-dimethoxyphenyl)spiro[4,4]nonane,
- 1-Oxa-6-oxo-7-(3,4,5-trimethoxyphenyl)methylene-2,9-di(3,4-dimethoxyphenyl)spiro[4,4]nonane
- 1-Oxa-6-oxa-7-dimethylmethylene-2,9-di(3,4-dimethoxyphenyl)-spiro[4,4]nonane,
- 1-Oxa-6-oxo-7-benzoyl-2,9-di(3,4-dimethoxyphenyl)-spiro[4,4]-nonane,
- 1-Oxa-6-hydroxy-2,9-di(3,4-dimethoxyphenyl)-spiro[4,4]nonane,
- 1-Oxa-6-(3,5-dinitro)benzoyloxy-2,9-di(3,4-dimethoxyphenyl)-spiro[4,4]nonane, or
- 1-Oxa-6-cyanomethylene-2,9-di(3,4-dimethoxyphenyl)spiro[4,4]nonane, or a salt of such a compound.

18. A pharmaceutical or veterinary formulation comprising a compound as claimed in claim 1 and a pharmaceutically or veterinarily acceptable carrier.

* * * * *